United States Patent
Zhang et al.

(10) Patent No.: US 11,519,041 B2
(45) Date of Patent: Dec. 6, 2022

(54) SIDWF1 GENE CONTROLLING INTERNODE LENGTH IN SESAME

(71) Applicant: Henan Sesame Research Center, Henan Academy Of Agricultural Sciences, Zhengzhou (CN)

(72) Inventors: Haiyang Zhang, Zhengzhou (CN); Hongmei Miao, Zhengzhou (CN); Chun Li, Zhengzhou (CN); Yinghui Duan, Zhengzhou (CN); Libin Wei, Zhengzhou (CN); Ming Ju, Zhengzhou (CN)

(73) Assignee: Henan Sesame Research Center, Henan Academy Of Agricultural Sciences, Zhengzhou (CN)

( * ) Notice: Subject to any disclaimer, the term of this patent is extended or adjusted under 35 U.S.C. 154(b) by 0 days.

(21) Appl. No.: 16/935,232

(22) Filed: Jul. 22, 2020

(65) Prior Publication Data

US 2020/0354799 A1     Nov. 12, 2020

Related U.S. Application Data

(63) Continuation-in-part of application No. PCT/CN2019/095271, filed on Jul. 9, 2019.

(30) Foreign Application Priority Data

May 10, 2019     (CN) .......................... 201910388525.X (51) Int. Cl.
    *C12Q 1/6895*     (2018.01)
(52) U.S. Cl.
    CPC ....... *C12Q 1/6895* (2013.01); *C12Q 2600/13* (2013.01); *C12Q 2600/156* (2013.01)
(58) Field of Classification Search
    None
    See application file for complete search history.

(56) References Cited

PUBLICATIONS

Zhang et al Genome sequencing of the important oilseed crop *Sesamum indicum* L. (2013) Genome Biology 14:401, 9 pages (Year: 2013).*
Wei, et al. Characterization of the sesame (*Sesamum indicum* L.) global transcriptome using Illumina paired-end sequencing and development of EST-SSR marker (2011) BMC Genomics 12:451, 13 pages (Year: 2011).*
NCBI BLAST (blast.ncbi.nlm.nih.gov)—SEQ ID No. 1 (Year: 2017).*
NCBI BLAST (blast.ncbi.nlm.nih.gov)—SEQ ID No. 2 (Year: 2017).*
NCBI BLAST (blast.ncbi.nlm.nih.gov)—SEQ ID No. 3 (Year: 2017).*
NCBI BLAST (blast.ncbi.nlm.nih.gov)—SEQ ID No. 4 (Year: 2017).*

* cited by examiner

*Primary Examiner* — Katherine D Salmon
(74) *Attorney, Agent, or Firm* — Georgi Korobanov (57) ABSTRACT

A Sidwf1 gene of Sesamum indicum, including two exons and an intron, is 1638 bp in total, and has a sequence represented by SEQ ID NO: 1. Also provided is a method for determining the internode length type in sesame samples, the method including: 1) extracting a genomic DNA of a sesame sample; 2) synthesizing three primers including SiSNPdwf1 F1, SiSNPdwf1 F2, and SiSNPdwf1 R; amplifying the Sidwf1 gene or an allele SiDWF1 thereof with the genomic DNA of the sesame sample as a template, with a combination of SiSNPdwf1 F1, SiSNPdwf1 F2, and SiSNPdwf1 R a combination of SiSNPdwf1 F1 and SiSNPdwf1 R, or a combination of SiSNPdwf1 F2 and SiSNPdwf1 R, as primers, thereby yielding a PCR product; and performing electrophoresis on the PCR product or sequencing the PCR product, and determining the phenotype of the sesame sample according to an electrophoresis or sequencing result.

2 Claims, 5 Drawing Sheets

Specification includes a Sequence Listing.

SEQUENCE LISTING

```
<160> NUMBER OF SEQ ID NOS: 9

<210> SEQ ID NO 1
<211> LENGTH: 1638
<212> TYPE: DNA
<213> ORGANISM: Artificial Sequence
<220> FEATURE:
<223> OTHER INFORMATION: Fully synthetic

<400> SEQUENCE: 1
atggcgggca gtaatgaagt aaatgtcaac gaatcaaagg taatcacgca tattttcttc      60
ctgggttcct cagaattctt ggtttctttg ttttgcggtg tggaattagg gtcttctccg     120
atgtgggttc ctgaatttc ttcgtttctt ctcttaattt tggggttaat agtggggttt      180
gtgatggttt tccaaagaag atttttatttg gaggaaagag ttgtgattta tggataaaga    240
ttgagtcttt tgcctttgat tttgagggtt tgggcagctg cttctctctc tctatatacc    300
```

```
tattttttgct attcgttctt tgccccctttt gttctcctct ttgttttttc tcgcccaata    360
ctgatttagc agtccccata aacctgtttt atgcttgttt gttgggttat ttttaggtgg    420
tttctccact tttccatttc cctttctttt tatagacttt catgttttc ttttcttttc    480 ggcgttttcc tttacagctg attacctta ctggatgttg atgatactga tttgggatgc    540
atttgatcaa atttcattct caatttcggt ttattttcta ttttgtgctg caattgatgg    600
ataaggaaac cattggtata ttgaaattga ctggctgtct ttatgcagag ggtggttcca    660
cttaatacat ggatccttat atccaacttc aagcttgctt acaacatgct tcggcggcct    720
gatggtacat ttaatcggga attgaacgag tttcttgacc ggaaagtgac tgcaaatgct    780
aatccagtag atggggttta ctcctttgat gttgtagatc gtgccacgag cctgcttaac    840
cgggtttatt tgaccgccca cgagaatgag cctcaacggg ggatcgtaga agtggaaaag    900
cccttgagta ccactgagat tgtgcctgtg attatattct tccacggtgg aagctttgtt    960
cattcctcag ccaacagtgc tatctatgac acgctctgtc gtcgcctcgt taatacttgc   1020
aaggcagcag ttgtatctgt gaattatcgt cgatcgtcag agcaccggta cccgtgtgcg   1080
tatgatgatg gatggaccgc tcttaattgg gttaactcga gatcatggct tcagagtggg   1140
aaggatcaga gagttcatat atatttggca ggcgatagtt ctggtggtaa tattgcgcat   1200
catgttgctc ttcgagctgc ggaggagggg gtcgaagtat tgggcaatat tcttcttcat   1260
cctttgtttg gtgggcagga gaggacagaa tctgagaaaa aattggatgg gaaatacttt   1320
gtaaggattc aagatagaga ttggtactgg agagcgtatt taccagaagg agaagatagg   1380
gaccatcctg cgtgtaatgt gtttggcccc aggagtagaa gcctcgaggg actaaaattt   1440
ccaaaaagcc ttgttgttgt ggctggatta gatcttcttc aggattggca attgcgttat   1500
gttgaagggc taagaaaatc agggcaagaa gtgaaactcc tttatctcga aaaggcaaca   1560
attgggttct atttcttgcc gaacaatgat catttccagt ccctgatgga tgagatgaaa   1620
agcttcatcc acccttaa                                                  1638
```

```
<210> SEQ ID NO 2
<211> LENGTH: 1029
<212> TYPE: DNA
<213> ORGANISM: Artificial Sequence
<220> FEATURE:
<223> OTHER INFORMATION: Fully synthetic

<400> SEQUENCE: 2
atggcgggca gtaatgaagt aaatgtcaac gaatcaaaga gggtggttcc acttaataca     60
tggatcctta tatccaactt caagcttgct tacaacatgc ttcggcggcc tgatggtaca    120
tttaatcggg aattgaacga gtttcttgac cggaaagtga ctgcaaatgc taatccagta    180
gatggggttt actcctttga tgttgtagat cgtgccacga gcctgcttaa ccgggtttat    240
ttgaccgccc acgagaatga gcctcaacgg ggatcgtag aagtggaaaa gcccttgagt    300
accactgaga ttgtgcctgt gattatattc ttccacggtg gaagctttgt tcattcctca    360
gccaacagtg ctatctatga cacgctctgt cgtcgcctcg ttaatacttg caaggcagca    420
gttgtatctg tgaattatcg tcgatcgtca gagcaccggt acccgtgtgc gtatgatgat    480
ggatggaccg ctcttaattg ggttaactcg agatcatggc ttcagagtgg aaggatcag    540 agagttcata tatatttggc aggcgatagt tctggtggta atattgcgca tcatgttgct    600
gttcgagctg cggaggaggg ggtcgaagta ttgggcaata ttcttcttca tcctttgttt    660
```

```
ggtgggcagg agaggacaga atctgagaaa aaattggatg ggaaatactt tgtaaggatt    720
caagatagag attggtactg gagagcgtat ttaccagaag gagaagatag ggaccatcct    780
gcgtgtaatg tgtttggccc caggagtaga agcctcgagg gactaaaatt tccaaaaagc   840
cttgttgttg tggctggatt agatcttctt caggattggc aattgcgtta tgttgaaggg    900
ctaaagaaat cagggcaaga agtgaaactc ctttatctcg aaaaggcaac aattgggttc   960
tatttcttgc cgaacaatga tcatttccag tccctgatgg atgagatgaa aagcttcatc   1020
caccccttaa                                                          1029
```

<210> SEQ ID NO 3
<211> LENGTH: 1638
<212> TYPE: DNA
<213> ORGANISM: Artificial Sequence
<220> FEATURE:
<223> OTHER INFORMATION: Fully synthetic

<400> SEQUENCE: 3

```
atggcgggca gtaatgaagt aaatgtcaac gaatcaaagg taatcacgca tattttcttc    60
ctgggttcct cagaattctt ggtttctttg ttttgcggtg tggaattagg gtcttctccg   120
atgtgggttc ctgaattttc ttcgtttctt ctcttaattt tggggttaat agtggggttt   180
gtgatggttt tccaaagaag attttatttg gaggaaagag ttgtgattta tggataaaga   240
ttgagtcttt tgcctttgat tttgagggtt tgggcagctg cttctctctc tctatatacc   300
tatttttgct attcgttctt tgccccctttt gttctcctct tgtttttttc tcgcccaata   360
ctgatttagc agtccccata aacctgtttt atgcttgttt gttgggttat ttttaggtgg   420
tttctccact tttccatttc cctttctttt tatagacttt catgttttttc ttttcttttc    480 ggcgttttcc tttacagctg attacccttta ctggatgttg atgatactga tttgggatgc   540
atttgatcaa atttcattct caatttcggt ttattttcta ttttgtgctg caattgatgg    600
ataaggaaac cattggtata ttgaaattga ctggctgtct ttatgcagag ggtgggttcca   660 cttaatacat ggatccttat atccaacttc aagcttgctt acaacatgct tcggcggcct   720
gatggtacat ttaatcggga attgaacgag tttcttgacc ggaaagtgac tgcaaatgct   780
aatccagtag atggggttta ctcctttgat gttgtagatc gtgccacgag cctgcttaac   840
cgggtttatt tgaccgccca cgagaatgag cctcaacggg ggatcgtaga agtgaaaaag   900
cccttgagta ccactgagat tgtgcctgtg attatattct tccacggtgg aagctttgtt   960
cattcctcag ccaacagtgc tatctatgac acgctctgtc gtcgcctcgt taatacttgc   1020
aaggcagcag ttgtatctgt gaattatcgt cgatcgccag agcaccggta cccgtgtgcg   1080
tatgatgatg gatggaccgc tcttaattgg gttaactcga gatcatggct tcagagtggg   1140
aaggatcaga gagttcatat atatttggca ggcgatagtt ctggtggtaa tattgcgcat   1200
catgttgctg ttcagctgcg ggaggagggg gtcgaagtat tgggcaatat tcttcttcat   1260
cctttgtttg gtgggcagga gaggacagaa tctgagaaaa aattggatgg gaaatacttt   1320
gtaaggattc aagatagaga ttggtactgg agagcgtatt taccagaagg agaagatagg   1380
gaccatcctg cgtgtaatgt gtttggcccc aggagtagaa gcctcgaggg gactaaaattt   1440 ccaaaaagcc ttgttgttgt ggctggatta gatcttcttc aggattggca attgcgttat   1500
gttgaagggc taaagaaatc agggcaagaa gtgaaactcc tttatctcga aaaggcaaca   1560
attgggttct atttcttgcc gaacaatgat catttccagt ccctgatgga tgagatgaaa   1620
agcttcatcc accccttaa                                                1638
```

<210> SEQ ID NO 4
<211> LENGTH: 1029
<212> TYPE: DNA
<213> ORGANISM: Artificial Sequence
<220> FEATURE:
<223> OTHER INFORMATION: Fully synthetic

<400> SEQUENCE: 4

```
atggcgggca gtaatgaagt aaatgtcaac gaatcaaaga gggtggttcc acttaataca    60
tggatcctta tatccaactt caagcttgct tacaacatgc ttcggcggcc tgatggtaca   120
tttaatcggg aattgaacga gtttcttgac cggaaagtga ctgcaaatgc taatccagta   180
gatggggttt actcctttga tgttgtagat cgtgccacga gcctgcttaa ccgggtttat   240
ttgaccgccc acgagaatga gcctcaacgg gggatcgtag aagtggaaaa gcccttgagt   300
accactgaga ttgtgcctgt gattatattc ttccacggtg gaagctttgt tcattcctca   360
gccaacagtg ctatctatga cacgctctgt cgtcgcctcg ttaatacttg caaggcagca   420
gttgtatctg tgaattatcg tcgatcgcca gagcaccggt acccgtgtgc gtatgatgat   480
ggatggaccg ctcttaattg ggttaactcg agatcatggc ttcagagtgg aaggatcag   540
agagttcata tatatttggc aggcgatagt tctggtggta atattgcgca tcatgttgct   600
gttcgagctg cggaggaggg ggtcgaagta ttgggcaata ttcttcttca tccttttgttt   660
ggtgggcagg agaggacaga atctgagaaa aaattggatg gaaatacttt tgtaaggatt   720
caagatagag attggtactg gagagcgtat ttaccagaag gagaagatag ggaccatcct   780
gcgtgtaatg tgtttggccc caggagtaga agcctcgagg gactaaaatt tccaaaaagc   840
cttgttgttg tggctggatt agatcttctt caggattggc aattgcgtta tgttgaaggg   900
ctaaagaaat cagggcaaga agtgaaactc ctttatctcg aaaaggcaac aattgggttc   960
tatttcttgc cgaacaatga tcatttccag tccctgatgg atgagatgaa aagcttcatc  1020
caccct taa                                                        1029
```

<210> SEQ ID NO 5
<211> LENGTH: 19
<212> TYPE: DNA
<213> ORGANISM: Artificial Sequence
<220> FEATURE:
<223> OTHER INFORMATION: Fully synthetic

<400> SEQUENCE: 5

```
ggggtggggt gaaagacaa                                                 19
```

<210> SEQ ID NO 6
<211> LENGTH: 20
<212> TYPE: DNA
<213> ORGANISM: Artificial Sequence
<220> FEATURE:
<223> OTHER INFORMATION: Fully synthetic

<400> SEQUENCE: 6

```
tcgccaacac aaatgacagg                                                20
```

<210> SEQ ID NO 7
<211> LENGTH: 25
<212> TYPE: DNA
<213> ORGANISM: Artificial Sequence
<220> FEATURE:
<223> OTHER INFORMATION: Fully synthetic

```
<400> SEQUENCE: 7
gtatctgtga attatcgtcg atagc                                              25

<210> SEQ ID NO 8
<211> LENGTH: 30
<212> TYPE: DNA
<213> ORGANISM: Artificial Sequence
<220> FEATURE:
<223> OTHER INFORMATION: Fully synthetic

<400> SEQUENCE: 8
ataatgtatc tgtgaattat cgtcgatagt                                         30

<210> SEQ ID NO 9
<211> LENGTH: 22
<212> TYPE: DNA
<213> ORGANISM: Artificial Sequence
<220> FEATURE:
<223> OTHER INFORMATION: Fully synthetic

<400> SEQUENCE: 9
ctctctgatc cttcccactc tg                                                 22
```

SiDWF1 GENE CONTROLLING INTERNODE LENGTH IN SESAME

CROSS-REFERENCE TO RELATED APPLICATIONS

This application is a continuation-in-part of International Patent Application No. PCT/CN2019/095271 with an international filing date of Jul. 9, 2019, designating the United States, now pending, and further claims foreign priority benefits to Chinese Patent Application No. 201910388525.X filed on May 10, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the field of molecular genetics and breeding of sesame, and more particularly to a Sidwf1 gene controlling the internode length of sesame and a method for breeding sesame varieties using the gene.

Sesame (*Sesamum indicum* L., 2n=26) is a specific oilseed crop with high oil quality. Sesame belongs to high-height crop. Most sesame varieties are uniculm with tall stem, which is not suitable for high density cultivation and mechanical harvesting. A sesame dwarf mutant Dw607 was successfully created by Henan Sesame Research Center, Henan Academy of Agricultural Sciences. China in 2009 using the ethyl methyl sulfonate (EMS) mutagenesis techniques. The height of the mutant varies from 120-150 cm with short internode length ranging from 3.8-4.6 cm and high capsule density.

SUMMARY

The disclosure extracts a Sidwf1 gene (the gene sequence is named SiGIB1D in the sesame genome) from a sesame mutant Dw607 with short internode length. The disclosure also provides an SNP marker of the Sidwf1 gene for facilitating screening and breeding of new sesame varieties.

The Sidwf1 gene is located on the 4th chromosome of sesame and is a recessive gene (the mutation site is located at the 1057$^{th}$ base of the wild-type gene controlling normal internode length), with a 100% explanation rate for the dwarf phenotype with short internode length (that is: the gene controls the short internode length phenotype). The Sidwf1 gene is 1638 bp in length and comprised of two exons and an intron. The sequence is represented by SEQ ID NO: 1.

The cDNA corresponding to the Sidwf1 gene has 1029 bp encoding 343 amino acids. A mutation occurred at the 448th nucleotide of the wild-type (wt.) gene (that is: the gene controls normal internode length), i.e., the base is mutated from C (wt.) to T (dwf). The base sequence of the cDNA is represented by SEQ ID NO: 2.

The allele SiDWF1 corresponding to the Sidwf1 gene is dominant and determines a normal internode phenotype in sesame varieties (that is, the allele controls the relative long internode phenotype). The allele SiDWF1 has a sequence represented by SEQ ID NO: 3.

The cDNA (the cDNA determining the normal internode length) corresponding to the allele SiDWF1 is the same as the DNA sequence of the dwarf mutant (presenting the short internode length phenotype) except that the 448th nucleotide in the cDNA sequence of the wild-type gene is C. The base sequence of the cDNA is represented by SEQ ID NO: 4.

The following primer pair is used to amplify the Sidwf1 gene or the allele SiDWF1:

```
                                        (SEQ ID NO: 5)
DWF1 Primer F: 5'- GGGGTGGGGTGAAAGACAA -3';

(SEQ ID NO: 6)
DWF1 Primer R: 5'- TCGCCAACACAAATGACAGG -3'.
```

A method for PCR amplification of the Sidwf1 gene or the allele SiDWF1, the method comprising:

(1) extracting sesame genomic DNA from the wild type with normal internode phenotype or a dwarf sesame variety Yuzhi Dw607; and (2) amplifying the Sidwf1 gene or the allele SiDWF1 thereof with the sesame genomic DNA extracted in (1) as a template with the primer pair.

The following single nucleotide polymorphism (SNP) primers are used to distinguish the Sidwf1 gene and the allele SiDWF1:

```
                                        (SEQ ID NO: 7)
SiSNPdwf1 F1:
5'- GTATCTGTGAATTATCGTCGATAGC -3';

(SEQ ID NO: 8)
SiSNPdwf1 F2:
5'- ATAATGTATCTGTGAATTATCGTCGATAGT -3';

(SEQ ID NO: 9)
SiSNPdwf1 R:
5'-CTCTCTGATCCTTCCCACTCTG -3'.
```

The combination of the primer SiSNPdwf1 F1 and SiSNPdwf1 R is used to detect whether the amplified product contains the allele SiDWF1 (wt.) of the Sidwf1 gene. The combination of the primer SiSNPdwf1 F2 and SiSNPdwf1 R is used to detect whether the amplified product contains the Sidwf1 gene (dwarf type).

To differentiate the SNP site of the target gene, the SNP primers are designed as follows:

(1) Three specific SNP primers are designed, with an introduction of a mismatched base at the 3rd position from the Y end of each specific SNP primer, to improve the specificity of the amplified product. The principle of introducing a mismatch as follows: the mismatched base at the 3rd position of the 3' end of the primer forms a complementary structure with the SNP site, that is, a strong mismatched type (C/T or G/A) matches a weak mismatched type (C/A or GT), and a medium mismatched type (A/A, C/C, G/G or TT) matches another medium mismatched type;

(2) In two forward or reverse primers containing the SNP site, additional 5 bases are randomly added to the 5' end of one of the primer sequences, in order to distinguish the PCR products at different sites in the gel electrophoresis.

A method for determining the internode length in sesame using the SNP primer pair comprises:

(1) extracting a genomic DNA of a sesame sample;

(2) synthesizing three primers comprising SiSNPdwf1 F1, SiSNPdwf1 F2, and SiSNPdwf1 R; amplifying a Sidwf1 gene or an allele SiDWF1 thereof with the genomic DNA of the sesame sample extracted in (1) as a template, with a combination of SiSNPdwf1 F1, SiSNPdwf1 F2, and SiSNPdwf1 R, a combination of SiSNPdwf1 F1 and SiSNPdwf1 R, or a combination of SiSNPdwf1 F2 and SiSNPdwf1 R, as primers, thereby yielding a PCR product;

(3) performing electrophoresis on the PCR product or sequencing the PCR product, and determining the phenotype of the sesame sample according to an electrophoresis or sequencing result:

3.1) when the PCR product is 121 bp in length, the sesame sample is a homozygous dominant phenotype with normal plant height and internode length trait;

3.2) when the PCR product is 126 bp in length, the sesame sample is a homozygous recessive phenotype with dwarf trait and short internode length trait; and 3.3) when the PCR product has two bands of 121 bp and 126 bp in length, the sesame sample is a heterozygous phenotype with normal plant height and internode length trait.

The disclosure also provides a method for applying the Sidwf1 gene in screening new varieties with the short internode length phenotype.

On the basis of obtaining the dwarf varieties with short internode length, in order to clone the gene controlling the internode length and to investigate the difference of gene sequences between the dwarf mutant Dw607 (dwf1) and the wild type (wt.), an F6 population of the cross derived from Dw607 (dwf1 type)×15N41 (wt.) has been constructed. Based on the population mapping, sesame reference genome map, and genome re-sequencing techniques. Sidwf1 gene sequence is obtained and annotated as SiGIB1D in the sesame genome. Identification of Sidwf1 gene in sesame supplies the solid foundation for studies of the mechanism of the growth and development regulation and new dwarf varieties breeding in sesame and other crops.

The following advantages are associated with the Sidwf1 gene of sesame according to embodiments of the disclosure:

(1) The disclosure provides a Sidwf1 gene controlling the short internode length of sesame, and develops a SNP marker SiSNPdwf1. Also, the disclosure provides a PCR amplification method for determining whether the sesame contains the Sidwf1 gene and the SNP site, which is convenient to distinguish the phenotype of varieties and the internode length of a sesame line.

(2) The Sidwf1 gene plays an active role in exploring the mechanism of growth and development in sesame and selecting the dwarf varieties resistant to lodging.

(3) The disclosure provides a method for identifying the Sidwf1 gene and the SNP marker SiSNPdwf1 and improving the efficiency of plant breeding and the research level of molecular genetics.

BRIEF DESCRIPTION OF THE DRAWINGS

lane M indicates DL2000 marker showing partial DNA bands of 250 bp and 100 bp from top down; lanes 1-10 indicate the dwarf phenotype with short internode of the $F_{2-3}$ population derived from a cross between dwarf mutant Dw607 and Yuzhi 11, wherein all of the samples contain only the Sidwf1 gene allele 1(i.e., dwf1 type).

lanes 11-20 indicate the normal type with normal internode length of the $F_{2-3}$ population derived from a cross between dwarf mutant Dw607 and Yuzhi 11, wherein the lanes 12, 13, 15, 16, 17, 19 and 20 contain Sidwf1 alleles 1 and 2, while the lanes 11, 14, 18 contain only Sidwf1 allele 1 (i.e. dwf1 type).

lane 21-40 indicate 20 sesame germplasm accessions with normal phenotype, wherein all of the lanes contain only the Sidwf1 gene allele 2 (wt.).

lane M indicates DL 2000 marker showing DNA bands 2000 bp, 1000 bp, 750 bp, 500 bp, 250 bp and 100 bp, from top down.

lane 1-10 indicate 20 germplasm accessions (with normal phenotype), wherein all of the lanes contain only the Sidwf1 gene allele 2 (wt.).

lanes 11-20 indicate the $F_{2-3}$ population derived from a cross between dwarf mutant Dw607 and Yuzhi 11, wherein the lanes 22, 27, and 30 contain only Sidwf1 allele 2 (wt.).

lanes 21, 23, 24, 25, 26, 28, and 29 contain Sidwf1 alleles 1 and 2.

lanes 31-40 indicate the $F_{2-3}$ population lines (dwarf phenotype with short internode) derived from a cross between dwarf mutant Dw607 and Yuzhi 11, wherein all of the lanes only contain Sidwf1 allele 1 (dwf1).

DETAILED DESCRIPTION OF THE EMBODIMENTS

To further illustrate the invention, embodiments detailing a Sidwf1 gene of sesame are described below. It should be noted that the following embodiments are intended to describe and not to limit the disclosure.

Sesame variety Yuzhi 11 is an important breeding material in China. The dwarf sesame mutant, Yuzhi Dw607, is a new variety bred from the progeny of the mutagenic sibling of Yuzhi 11 by Henan Sesame Research Center, Henan Academy of Agricultural Sciences. China. The dwarf sesame mutant Yuzhi Dw607 is characterized by the short internode length and high capsule density traits. The main traits of Yuzhi Dw607 are as follows: the average internode length ranging from 3.8-4.6 cm, three flowers per leaf axil, single stem, four-edge capsule, and white seed coat color.

Sesame variant 15N41 employed in the examples of the disclosure presents normal internode length, single flower per leaf axillary, branch, quadrilateral capsule and black seed coat color. The sesame variant 15N41 and other germplasm accessions, such as the sesame variety Yuzhi 11 described in the examples, are chosen for research. These germplasm accessions are available from the germplasm reservoir of Henan Sesame Research Center, Henan Academy of Agricultural Sciences, or other germplasm banks.

Example 1

1. Analysis of the Genetic Background of Internode Length Trait

The positive and reciprocal crosses between the mutant Dw607 with short internode and the germplasm materials with normal internode such as Yuzhi 11 and 15N41 were performed in 2012 (the cross combination shown in Table 1 below). The phenotype of internode length trait in $F_1$ progeny of the crosses was investigated.

Figure 1:
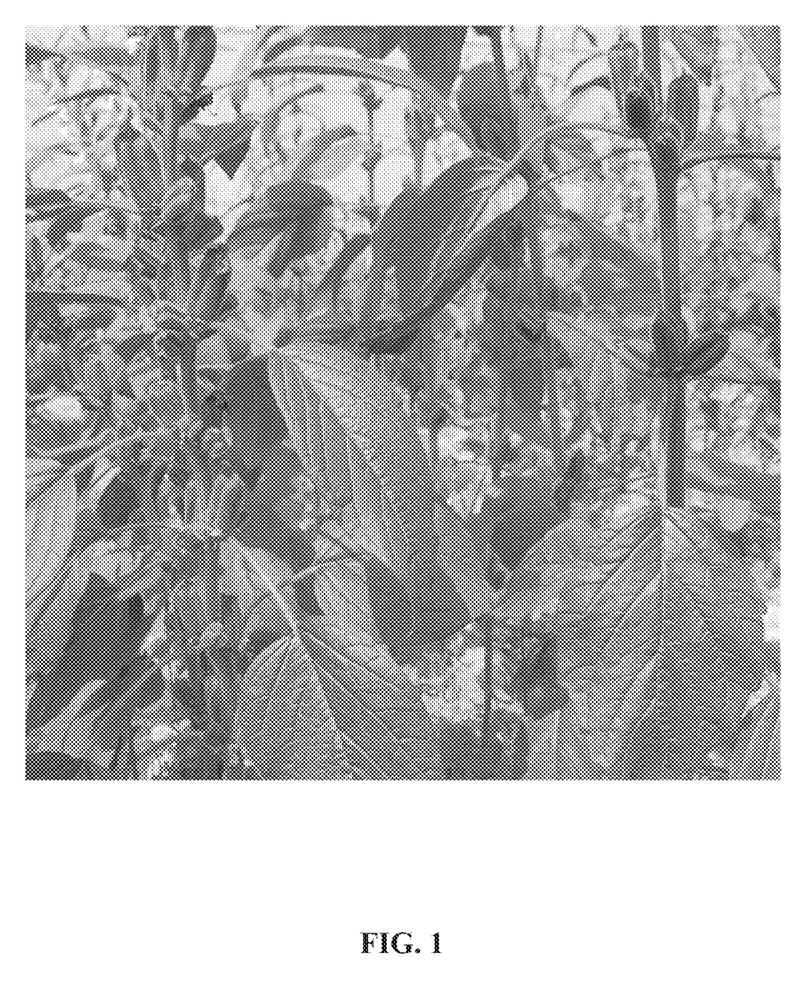
FIG. 1 shows the images of sesame dwarf mutant Dw607 (dwf1 type, left) with short internode length and its parent variety Yuzhi 11 (wild type, right) with normal internode length in a field.

The phenotypic differences between the mutant Dw607 and the parent Yuzhi 11 with normal internode were shown in FIG. 1. The statistical results in detail were shown in Table 1 below, where $\chi^2_{(0.05,\ 1)}=3.84$; '*' indicates the internode length less than 5.0 cm as short internode length; the internode length larger than 5.0 cm as normal internode length.

2. Construction of F2 Population Using the Short Internode Sesame and the Normal Internode Sesame as Parents A recombination inbred line (RIL) population was constructed using the short internode mutant Dw607 and the sesame variant 15N41 from 2013 to 2016. In 2016, the $F_6$ seeds of the RIL population were sowed in nutrition pots at Sanya experimental station of Henan Sesame Research Center, Henan Academy of Agricultural Sciences. The size of the population was larger than 600.

3. Mapping of Sidwf1 Gene (1) Genome Re-Sequencing of Parents and the 113 Individuals of $F_6$ Population On the basis of the preparation, the 113 individual $F_6$ plants were chosen from the RIL population. Young leaves of the 113 individual plants and the 2 parents were collected for DNA extraction according to the improved method of Wei et al. (2008). Illumina sequencing method was used to re-sequence the genomes of the 115 samples with the sequencing coverage ≥30×.

(2) The sequencing data of each sample was aligned using the sesame reference genome data and BWA package.

(3) During the final flowering of sesame, the internode length trait of the 113 individual $F_6$ plants and the 2 parental plants was measured.

Based on the genomic and phenotypic data of the $F_6$ population, the P-value of the variants associated with the internode length trait in sesame was calculated using the software Tassele 5.0. The detailed results were shown in FIG. 2.

Figure 2:
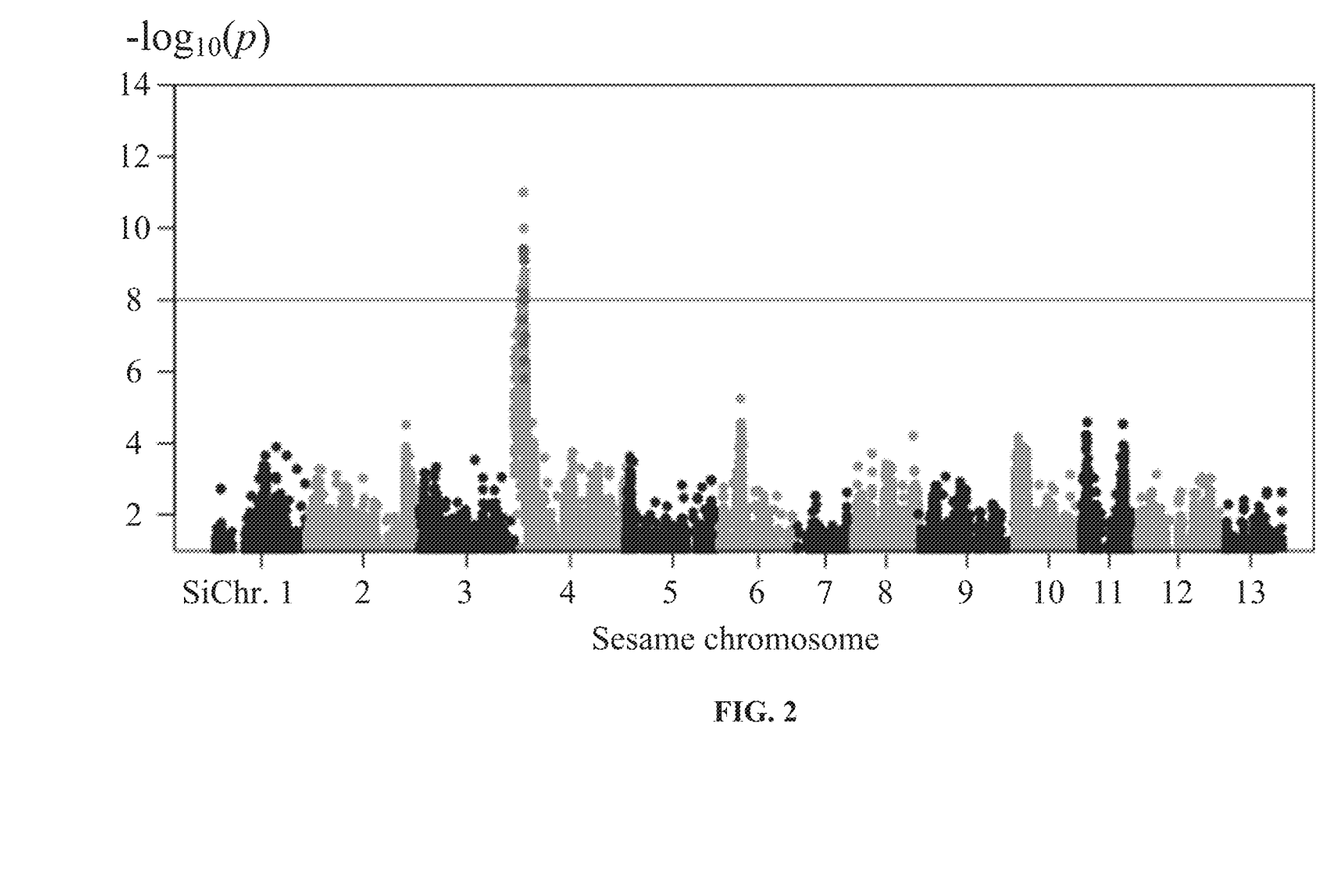
FIG. 2 is the location of the candidate SNP sites of the dwarf gene associated with the short internode length based on the association analysis of hybrid population in sesame.

The results showed that a variant with the lowest P-value was located on the fourth chromosome. All of the variants within the flanking region covering the upstream 200 Kb and

TABLE 1

Crosses and phenotype statistics of sesame population

| Parental combination | | Number of plants with normal internode/Number of plants with short internode* | | | | Theoretical ratio | |
|---|---|---|---|---|---|---|---|
| Parent 1 | Parent 2 | | BC$_1$ | | F$_2$ | | |
| (dwf1) | (wt.) | F$_1$ | ($\chi^2$ value) | BC$_2$ | ($\chi^2$ value) | BC$_1$ | F$_2$ |
| Dw607 | 15N41 | 281/0 | 78/72 (0.1667) | 110/0 | 132/48 (0.1852) | 1:1 | 3:1 |
| Dw607 | Yuzhi 11 | 260/0 | 188/198 (0.2098) | 245/0 | 202/61 (0.3363) | 1:1 | 3:1 |

The results showed that the $F_1$ progeny presented the normal phenotype of plant height and internode length, suggesting that the mutated trait is controlled by single nuclear recessive gene. The $F_2$ progeny in all field experiments were undertaken for trait investigation during the mature period. The results showed that the segregation ratio of the dwarf and short internode length trait in the mutant and the wild type accorded with 1:3, suggesting that the mutated trait is controlled by single recessive gene. Further investigation results of the back-cross population showed that the mutated trait in the progeny fitted with the expected ratio of 1:1 and demonstrated that the short internode length trait is controlled by single recessive gene.

the downstream 200 Kb segments were analyzed. Further analysis showed that 58 polymorphic SNP/InDel sites were included in the region, with P-value ranging from 9.08E-05 to 2.59E-15.

Further, the variants were screened using a variant database of 824 sesame germplasm accessions, and 12 variants were retained shown in FIG. 2 (green dots).

Further, the 12 variants were screened using the variant data of two bulked pools of $F_{2-3}$ population derived from dwarf mutant Dw607×Yuzhi 11. The results showed that only the locus C9_6989486 was significantly associated with the dwarf trait (the results were shown in Table 2 below).

TABLE 2

Information of the variants significantly associated with the internode length trait in sesame

| Variant name | Chromosome location | Contig (Scaffold) location | Variation type | | | |
|---|---|---|---|---|---|---|
| | | | Wild type | dwf1 type | Located gene | Variant location |
| C9_6958525 | SiChr.4 | 6958525 | T | TA | / | Intergenic region |
| C9_6986819 | SiChr.4 | 6986819 | G | GA | / | Intergenic region |
| C9_6989486 | SiChr.4 | 6989486 | C | T | C9.scaffold2.572 | 2$^{nd}$ exon |
| C9_7080799 | SiChr.4 | 7080799 | T | TA | / | Intergenic region |
| C9_7225874 | SiChr.4 | 7225874 | TTATA | TTATATA, T, TTA | / | Intergenic region |

Example 2

On the basis of Example 1, the disclosure further provides the analysis information of target gene cloning and sequencing. The processes were introduced as follows:

Based on the obtained variants in Example 1, the SNP C9_6989486 was determined as the target SNP site using the genome data of Yuzhi 11, and the located geneC9. scaffold2.572 was named Sidwf1. Sequence analysis detected that the gene was annotated as SiGIB1D gene in sesame genome (var. Yuzhi 11).

Subsequently, to amplify the sequence of Sidwf1 gene controlling internode length in sesame, a primer pair was designed using the software Primer premier 5.0 based on the genome data.

The following PCR primer pair was used to amplify the Sidwf1 gene:

```
                                        (SEQ ID NO: 5)
SiDWF1 F: 5'- GGGGTGGGGTGAAAGACAA -3';

(SEQ ID NO: 6);
SiDWF1 R: 5'- TCGCCAACACAAATGACAGG -3'.
```

Furthermore, PCR reaction was performed using the DNA of dwarf mutant Dw607 as PCR template (DNA extraction method referred in Example 1) and the above primer pairs.

PCR reaction was performed on a PTC 100 Thermal Cycler (MJ Research Inc.). Reaction condition was designed as follows: Pre-denaturation at 94° C. for 3 min, denaturation at 94° C. for 30 sec; 30 cycles with denaturation at 94° C. for 30 sec, annealing at 55° C. for 30 sec, and extension at 72° C. for 1 min; and final extension at 72° C. for 5 min. Finally, the PCR products were preserved at 4° C.

The amplified products were purified and sequenced (Tianjin Biochip Technology Co., Ltd.). The results showed that the full-length genome sequence of the Sidwf1 gene is 1638 bp containing 2 exons and 1 intron. The base sequence is represented by SEQ ID NO: 1.

Further, the genome DNA of Yuzhi 11 with normal internode trait was applied as a template to amplify the gene SiDWF1 controlling normal internode length using the above primers. The amplified gene SiDWF1 was sequenced and represented by SEQ ID NO: 3.

Figure 3:
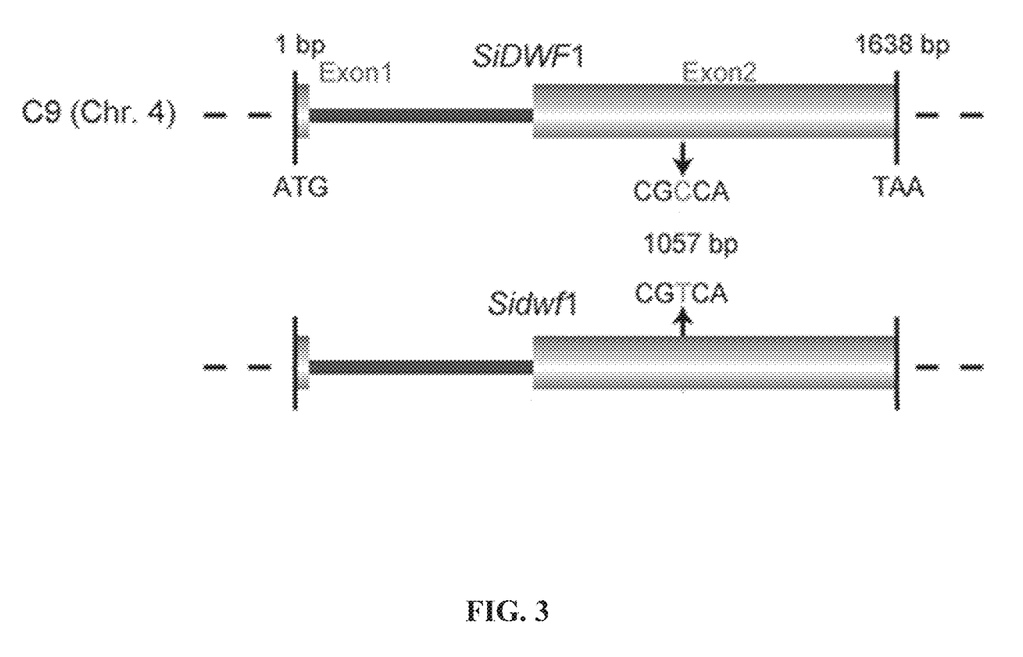
FIG. 3 is a schematic diagram of the structure of Sidwf1 gene of the invention. Boxes indicate exons, and black lines between boxes indicate introns. The base in red indicated by an arrow is the SNP site in the DNA sequences of Sidwf1 gene and the allele SiDWF1.

The gene Sidwf1 sequence was aligned to the allele SiDWF1 sequence, as shown in FIG. 3.

The gene Sidwf1 sequence was the same with the allele SiDWF1 except the 1057th base of the gene Sidwf1 sequence mutated from C to T. When the 1057th base is mutated from C to T, the 150th amino acid of an encoded protein was mutated from proline (P) to serine (S) and results in a change of the normal internode length to short type (dwf1 type).

Example 3

Based on the results of Example 2, to determine whether Sidwf1 gene is the target gene regulating the internode length in sesame, SNP primers were designed. Six hundred germplasm accessions and an F$_2$ population were applied to validate the SNP site. The processes were introduced as follows:

The following three SNP primers are used to distinguish the Sidwf1 gene and the allele SiDWF1:

```
                                        (SEQ ID NO: 7)
SiSNPdwf1 F1 sequence:
5'- GTATCTGTGAATTATCGTCGATAGC -3';

(SEQ ID NO: 8)
SiSNPdwf1 F2 sequence:
5'- ATAATGTATCTGTGAATTATCGTCGATAGT -3';

(SEQ ID NO: 9)
SiSNPdwf1 R sequence:
5'-CTCTCTGATCCTTCCCACTCTG -3'.
```

The following two rules should be considered before designing a SNP primer pair for detecting the SNP alleles in sesame varieties:

(1) Three specific SNP primers are designed, with an introduction of a mismatched base at the 3rd position from the 3' end of each specific SNP primer, in order to improve the specificity of the amplified products. The principle of introducing a mismatch is as follows: the mismatched base at the 3rd position from the 3' end of the primer can form a complementary structure with the SNP site, that is, a strong mismatched base (C/T or GA) matches a weak mismatched base (C/A or G/T), and a medium mismatched base (A/A, C/C, G/G or TT) matches another medium mismatched base.

(2) For the two forward primers containing the SNP site, 5 bases are randomly added to the 5'end of one of the primer sequences, which is convenient to distinguish the PCR product containing different SNP alleles in the subsequent gel electrophoresis.

600 individual plants were randomly chosen from the F$_{2-3}$ population derived from Dw607×Yuzhi 11, and the internode length type of each individual plantlet in the field was investigated. Young leaves of 600 individual plants and 2 parents were collected and the genomic DNA was extracted using the modified CTAB method (refers to Example 1).

The extracted genomic DNAs were employed as the template to perform PCR reaction using the three SNP primers (i.e. a combination of the primer SiSNPdwf1 $F_1$ and the primer SiSNPdwf1 R or a combination of the primer SiSNPdwf1 F2 and the primer SiSNPdwf1 R).

10 μL of PCR reaction system comprised:
Template DNA (50 ng/μL), 1.0 μL;
10×PCR Buffer ($Mg^{2+}$), 1.0 μL;
Taqase enzyme (5 U/μL), 0.2 μL:
dNTP (10 mmol/L), 0.2 μL;
Forward Primer 1(10 μM), 0.5 μL;
Forward specific Primer 2 (10 μM), 0.5 μL:
Reverse Primer (10 μM), 1.0 μL;
Ultrapure water, 5.6 μL PCR reaction was performed on a PTC 100 Thermal Cycler (MJ Research Inc.). PCR condition was recommended as follows: 94° C. for 3 min, 30 cycles of 30 s at 94° C., 30 s at 55° C., 30 s at 72° C., and a final 5 min extension at 72° C. PCR products were preserved at 4° C.

The PCR product was analyzed by non-denaturing polyacrylamide gel electrophoresis, where the gel concentration was 8-10%, the gel size was 180 mm×120 mm×2 mm, the electrophoresis buffer was 0.5×TBE, and the electrophoresis was performed at 150V constant voltage for 1.5-2 h.

After the electrophoresis, the gel was stained with silver nitrate, 0.1% (w/v) aqueous solution, and place on a horizontal shaker for 10 min for a deeper silver penetration. Addition of mixed solution containing 2% sodium hydroxide and 0.4% formaldehyde, the gel was placed on a horizontal shaker to develop a moderate color. The gel was rinsed repeatedly with deionized water and the data was recorded.

Figure 4:
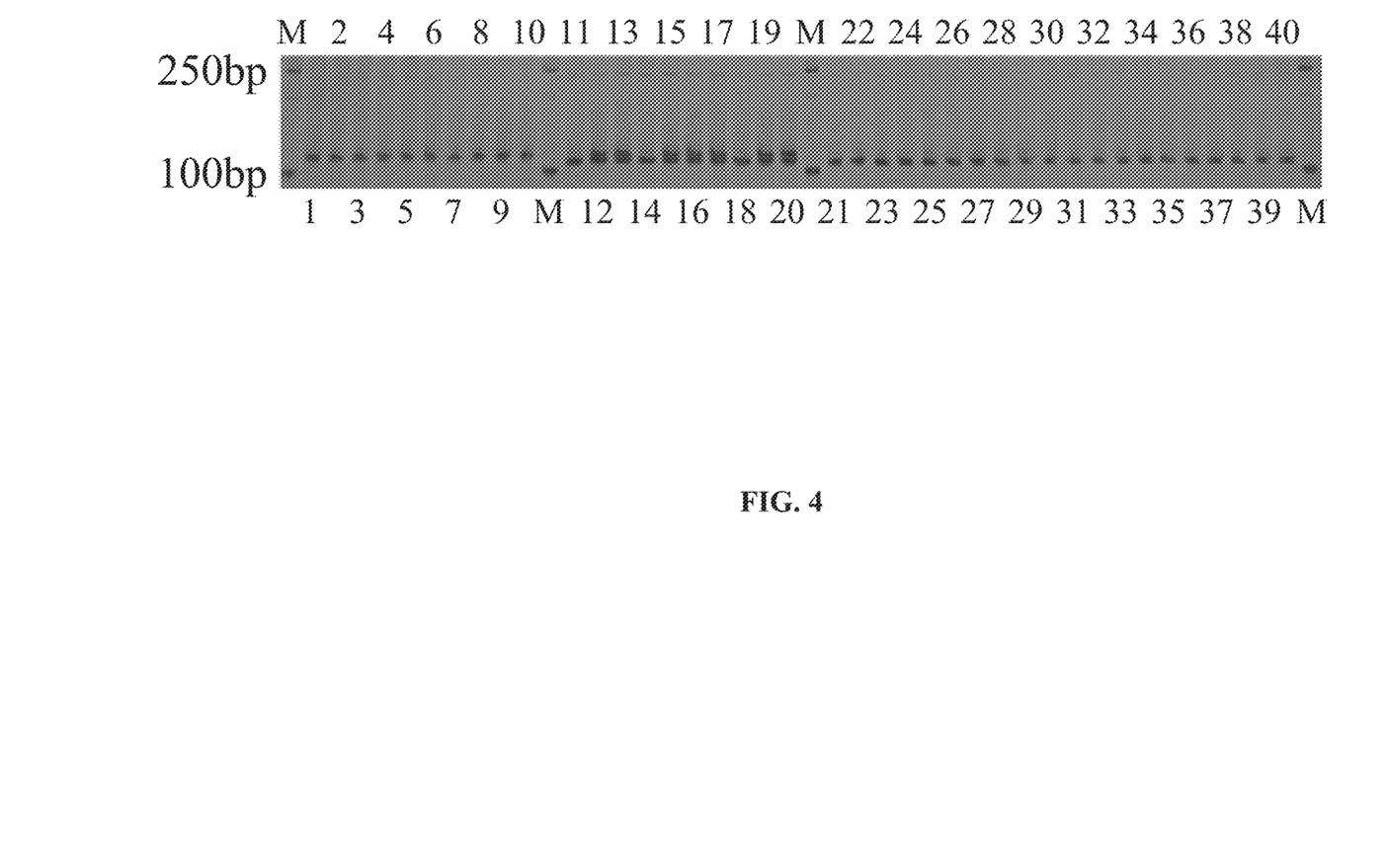
FIG. 4 is the PCR amplification of some sesame germplasm accessions using the forward primer pairs SiSNPdwf1 F1 and SiSNPdwf1 F2 and the reverse primer SiSNPdwf1 R designed for the SNP marker SiSNPdwf1 associated with the dwarf and short internode length trait, where.

Part of the electrophoresis results were shown in FIG. 4. The results showed that plants with short internode length phenotype had the amplicon with a band size of 126 bp, parent plants with normal internode length phenotype had the amplicon with a band size of 121 bp, and hybrid plants had amplicons with band sizes of 126 bp and 121 bp and the phenotype was normal internode length.

The results showed that the gene Sidwf1 was a gene that controls the internode length in sesame, which can be used to investigate the regulation mechanism of plant height and internode length traits in sesame and other crops.

Example 4

One hundred plant samples were chosen randomly from a hybrid offspring of Dw607 and Yuzhi 11, and another 100 plant samples were chosen from germplasm bank for breeding (the plant height and the internode length types were determined during flowering stage).

Genomic DNA of each of 200 plantlets was extracted and applied for PCR amplification using the three SNP primers disclosed in Example 3 to evaluate the reliability of SNP markers.

After PCR amplification, the PCR products of 121 bp were amplified using the forward primer 1 and the reverse primer, and the PCR products of 126 bp were amplified using the forward primer 2 and the reverse primer.

Figure 5:
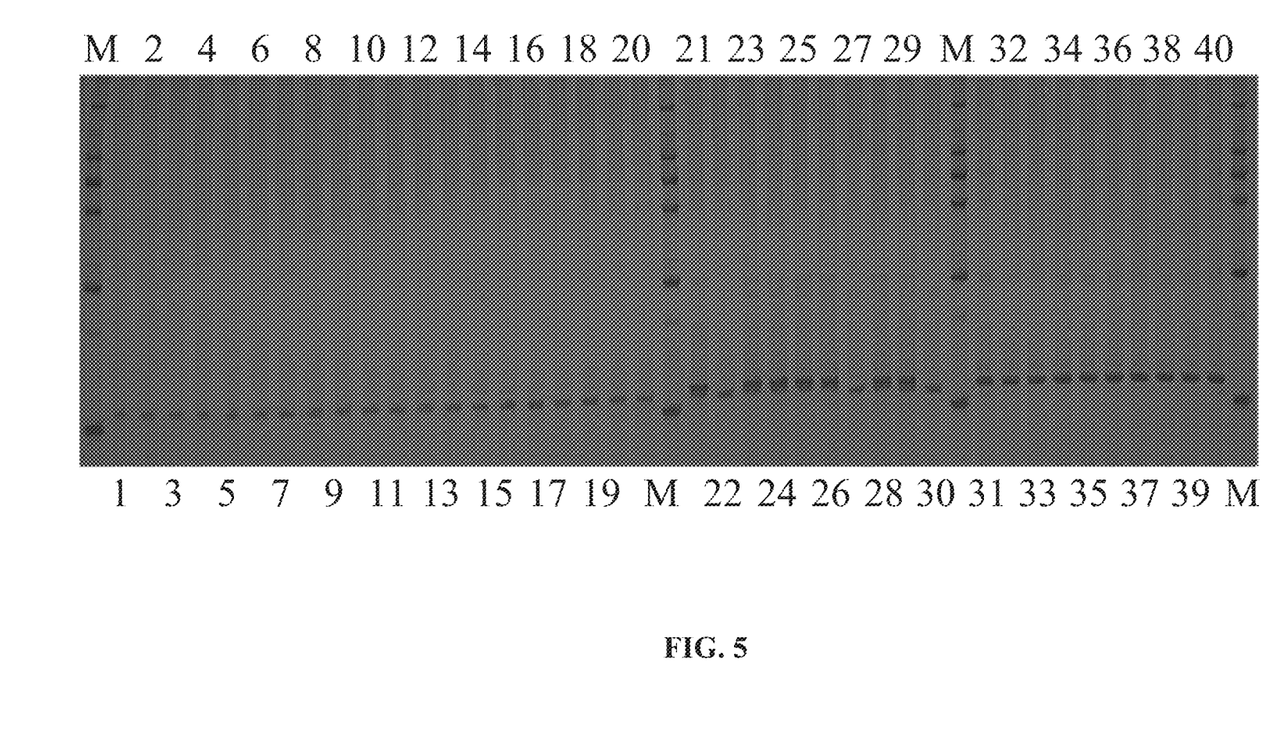
FIG. 5 is the PCR amplification of the sesame germplasm accessions using the primers of the dwarf SNP marker SiSNPdwf1, where.

Further, the PCR products were subjected to the gel electrophoresis, part results were shown in FIG. 5.

The selection results of the SiSNPdwf1 locus in the disclosure showed that the sesame plants containing the SiSNPdwf1 allele 1 (a band of 121 bp, i.e. the SiSNPdwf1 site in the disclosure) should exhibit normal internode length. The sesame plants containing SiSNPdwf1 allele 2 (a band of 126 bp, with a base mutated from C to T at the SiSNPdwf1 site) should exhibit short internode length. The sesame plants containing SiSNPdwf1 alleles 1 and 2 (121 bp and 126 bp, respectively) were heterozygous and should exhibit normal internode length.

The results indicated that all of the plantlets containing SiSNPdwf1 allele 1 (with a 121 bp band) are normal in internode length, with a reliability of 100%; all of the sesame plants containing SiSNPdwf1 allele 2 (with a 126 bp band) exhibited short internode length, with a reliability of 100%; all of the plantlets containing SiSNPdwf1 alleles 1 and 2 (with 121 bp and 126 bands) are also normal in internode length, with a reliability of 100%.

The experimental results showed that the SNP marker described in the disclosure was a genetic marker associated with the short internode length trait and can be used to predict the plant height and internode length type, to apply in molecular marker assisted breeding, and to breed new varieties with short internode length in sesame.

It will be obvious to those skilled in the art that changes and modifications may be made, and therefore, the aim in the appended claims is to cover all such changes and modifications.

What is claimed is:

1. A cDNA of an Sidwf1 gene of Sesamum indicum, the cDNA having a sequence consisting of cDNA SEQ ID NO:2.

2. A cDNA of an SiDWF1 gene of Sesamum indicum, the cDNA having a sequence consisting of SEQ ID NO:4.

* * * * *